US00PP23477P3

(12) United States Plant Patent
Hamilton et al.

(10) Patent No.: US PP23,477 P3
(45) Date of Patent: Mar. 19, 2013

(54) RASPBERRY PLANT NAMED 'DRISRASPTHREE'

(50) Latin Name: ***Rubus idaeus* L.**
Varietal Denomination: DrisRaspThree

(75) Inventors: Brian K. Hamilton, Richmond, TX (US); Miguel H. Ahumada, Ojai, CA (US); Richard E. Harrison, Aptos, CA (US); Lluvia V. Gutierrez, Salinas, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 13/066,358

(22) Filed: Apr. 13, 2011

(65) Prior Publication Data

US 2012/0266338 P1 Oct. 18, 2012

(51) Int. Cl.
*A01H 5/00* (2006.01)

(52) U.S. Cl. ..... Plt./204

(58) Field of Classification Search ..... Plt./204
See application file for complete search history.

*Primary Examiner* — Kent L Bell
(74) *Attorney, Agent, or Firm* — Jondle & Associates, P.C.

(57) ABSTRACT

A new and distinct variety of raspberry plant named 'DrisRaspThree' particularly distinguished by having high yield, good flavor, and a vigorous plant habit, is disclosed.

2 Drawing Sheets

Genus and species: *Rubus idaeus* L.
Variety denomination: 'DrisRaspThree'.

BACKGROUND OF THE NEW PLANT

The present invention relates to a new and distinct raspberry variety designated 'DrisRaspThree' and botanically known as *Rubus idaeus* L. This new raspberry variety was discovered in Santa Cruz, Calif. in October 2003 and originated from a cross between the proprietary female parent raspberry plant 'X146.7' (unpatented) and the proprietary male parent raspberry plant 'S858.1' (unpatented). The original seedling of the new variety was first asexually propagated by tissue culture at a nursery in Santa Cruz, Calif. 'DrisRaspThree' was subsequently asexually propagated by root cuttings and underwent further testing at a nursery in Santa Cruz, Calif. for four years. The present invention has been found to be stable and reproduce true to type through successive asexual propagations.

SUMMARY OF THE INVENTION

The following are the most outstanding and distinguishing characteristics of this new variety when grown under normal horticultural practices in Santa Cruz, Calif.:

1. High yield;
2. Good flavor; and
3. Vigorous growth habit.

DESCRIPTION OF THE PHOTOGRAPHS

This new raspberry plant is illustrated by the accompanying photographs which show fruit of the plant as well as the primocanes. The colors shown are as true as can be reasonably obtained by conventional photographic procedures. The photographs are of plants that are six months old.

DESCRIPTION OF THE NEW VARIETY

Figure 1:
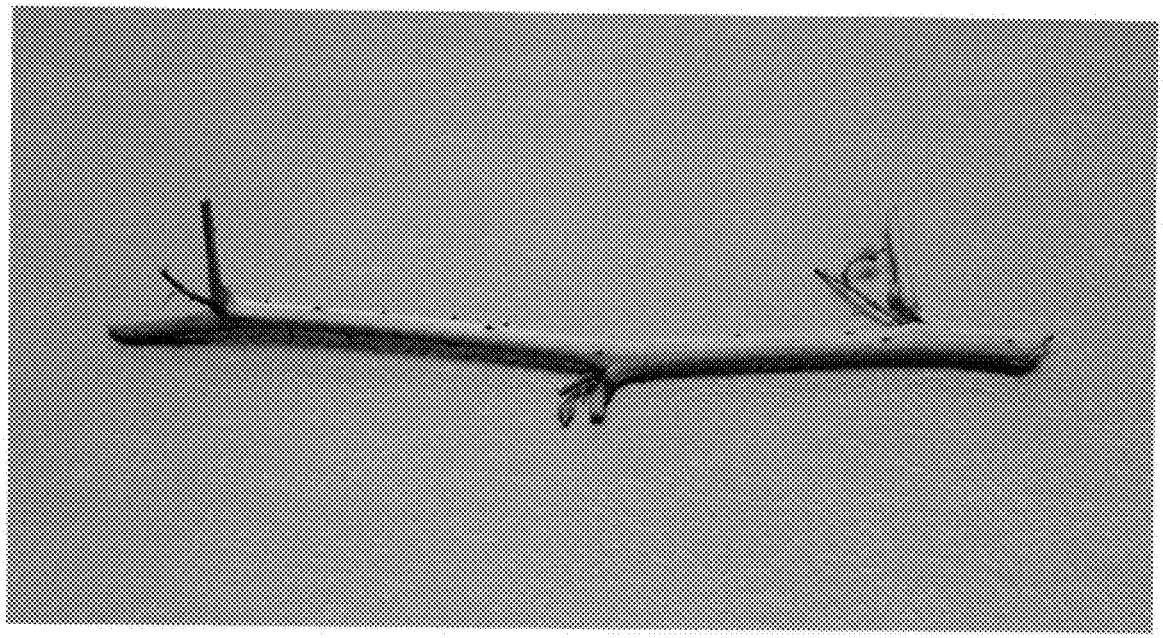
FIG. 1 shows a section of a young cane with prickles.
Figure 2:
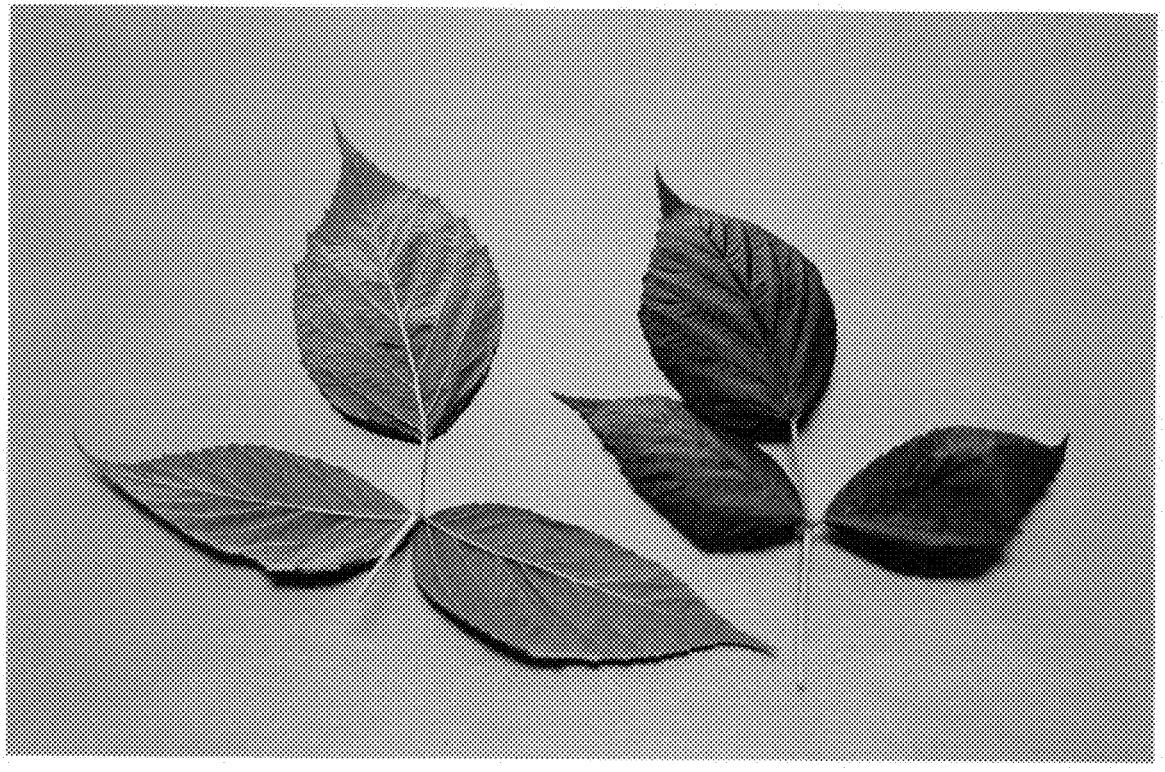
FIG. 2 shows both the upper surface and the lower surface of the plant leaves.
Figure 3:
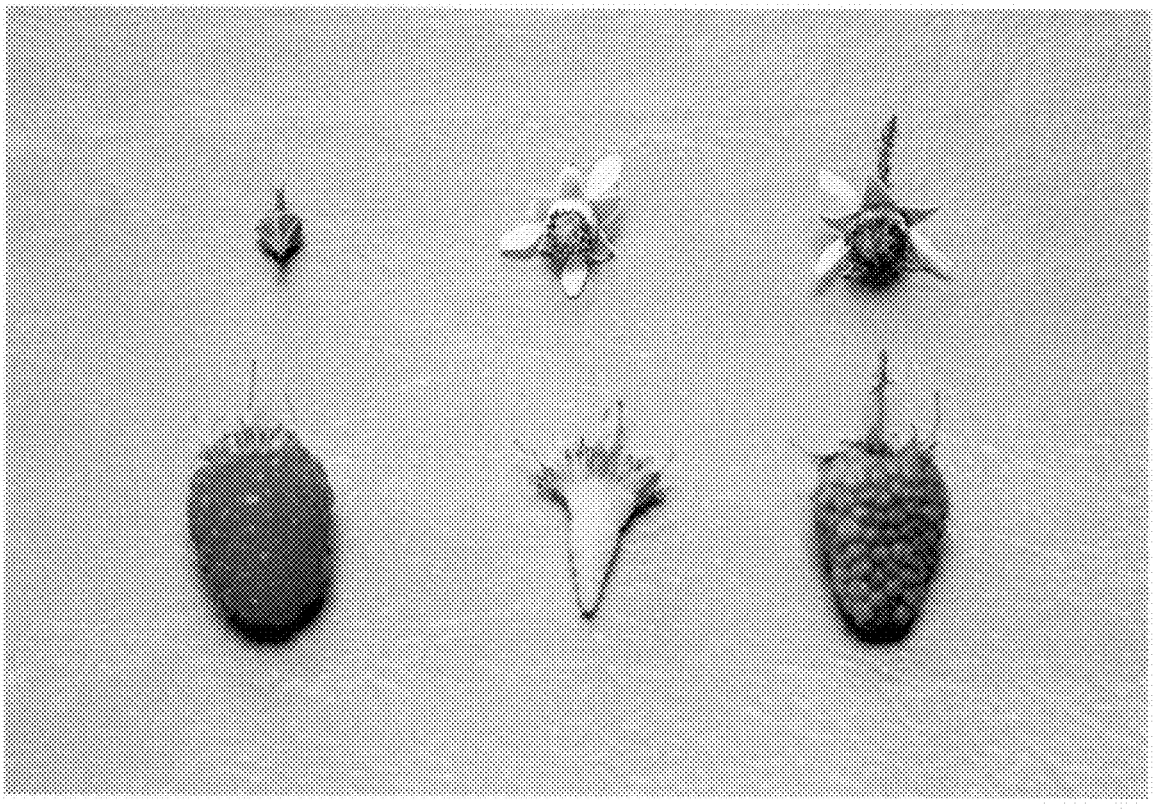
FIG. 3 shows close-up views of typical flowers and fruit at various stages of development.

The following description of 'DrisRaspThree' is based on observations taken from the 2005 to 2009 growing seasons in Santa Cruz, Calif. This description is in accordance with UPOV terminology. Color designations, color descriptions, and other phenotypical descriptions may deviate from the stated values and descriptions depending upon variation in environmental, seasonal, climatic and cultural conditions. 'DrisRaspThree' has not been observed under all possible environmental conditions. Color references are primarily to The R.H.S. Colour Chart of The Royal Horticultural Society of London (R.H.S.), Fifth Edition (2007).

DETAILED BOTANICAL DESCRIPTION

Classification:
- *Family*.—Rosaceae.
- *Botanical*.—*Rubus idaeus* L.
- *Common name*.—Raspberry.
- *Variety name*.—'DrisRaspThree'.

Parentage:
- *Female parent*.—The proprietary raspberry plant 'X146.7' (unpatented).
- *Male parent*.—The proprietary raspberry plant 'S858.1' (unpatented).

Plant:
- *Propagation*.—Tissue culture and root cuttings.
- *Size*.—Large.
- *Height*.—22.5 cm.
- *Width*.—20.5 cm.
- *Length/width ratio*.—1.1.
- *Productivity*.—High.
- *Self-fruitfulness*.—Self-fruitful.
- *New cane growth habit*.—Erect or upright.

Primocanes:

*Number of canes*.—Few.

*Glaucosity (waxy bloom) on full grown shoot after picking*.—Medium.

*Cane length*.—Long.

*Cane length for current season's cane in Autumn*.—209.20 cm.

*Length of internode*.—Medium.

*Cane diameter at central ½ cane*.—11.8 mm.

*Internodal distance at central ⅓ of cane*.—5.15 cm.

*Length of vegetative bud*.—Short.

*Number of young shoots*.—2.

*Anthocyanin coloration of apex during rapid growth*.—Present.

*Color*.—RHS 143C (Medium green).

*Intensity of anthocyanin coloration of apex during rapid growth*.—Weak.

*Time of young shoot emergence from the soil*.—Medium.

*Time of beginning of flowers*.—Medium; July 1.

*Time of beginning of fruit ripening in autumn*.—Medium; August 1.

*Length of fruiting period in autumn*.—Long; 4 months.

*Percent of cane flowering as primocane*.—50%.

*Percent primocane yield of total yield*.—50%.

*Glaucosity (waxy bloom) on current years cane in autumn*.—Medium.

*Cane strength*.—Strong.

*Shape of cane cross section*.—Rounded.

*Pubescence on canes*.—Present.

Floricanes:

*Dormant cane length in summer*.—Long.

*Dormant cane color in summer*.—RHS 165B (Medium greyed-orange).

*Dormant cane internode length (on central ½ cane)*.—5.0 cm.

*Fruiting lateral attitude*.—Horizontal to drooping.

*Fruiting lateral length*.—Semi-erect.

*Time of vegetative bud burst*.—Medium.

*Time of beginning of flowers*.—Medium; March 15.

*Time of beginning of fruit ripening*.—Medium; May 15.

*Length of fruiting period*.—Long; 3 months.

Prickles (spines):

*Density of spines on central third*.—Medium, 7 per cm on young laterals.

*Size of base of prickles*.—Small.

*Length (from base to tip)*.—Long.

*Length at 1.0 m height at end of harvest season (from base to tip)*.—1.9 mm.

*Width (on central ⅓ cane)*.—2.7 mm.

*Color (pigmentation)*.—RHS 187C (Dark greyed-purple).

*Attitude of tip*.—Horizontal.

*Size*.—Large.

*Texture*.—Soft.

*Presence and distribution on petioles*.—Present and irregularly distributed.

Leaves:

*Terminal leaflet*.—Length: Medium, 12.8 cm. Width: Narrow, 10.5 cm. Length/width ratio: 1.2. Leaf color: Upper surface: RHS 137A (Medium green). Lower surface: RHS 148B (Medium yellow-green). Venation pattern: Reticulate. Profile in cross section: Flat (straight). Relief between the veins: Strong. Overlapping of leaflets: Free. Glossiness: Medium. Shape: Ovate. Apex: Emarginate. Base: Obtuse. Margin: Crenate. Arrangement: Simple.

*Lateral leaflets (basal pair)*.—Number of leaflets: Usually 3. Size: Length: 10.5 cm. Width: 7.1 cm. Length/width ratio: 1.5. Venation pattern: Reticulate. Arrangement: Compound-opposite. Shape: Ovate. Apex: Emarginate. Base: Obtuse. Margin: Crenate. Lateral leaflet (length to stalklet, lower pair): Short.

*Rachis length between terminal leaflet and adjacent lateral leaflets*.—4.2 mm.

*Rachis color*.—RHS 144A (Medium yellow-green).

*Petiole*.—Size: Length: 7.4 cm. Diameter: 1.5 mm. Pigmentation: Upper surface: RHS 144A (Medium yellow-green). Lower surface: RHS 143C (Medium green).

*Petiolule*.—Size: Length: 2.3 mm. Diameter: 1.9 mm. Color: RHS 144A (Medium yellow-green).

Stipules:

*Orientation*.—Erect.

*Number per leaf*.—2.

*Size*.—Length: 11.7 mm. Diameter: 0.2 mm.

*Color*.—RHS 144B (Medium yellow-green).

Flowers:

*Size*.—Large.

*Diameter*.—3.84 cm.

*Petal number*.—5.

*Petal color*.—RHS 155D (White).

*Petal length*.—0.97 cm.

*Petal width*.—0.45 cm.

*Petal shape*.—Round.

*Petal apex*.—Round.

*Petal base*.—Concave — convex.

*Petal margin*.—Smooth.

*Sepal number*.—5.

*Sepal color*.—RHS 144A (Medium yellow-green).

*Sepal length*.—14.1 mm.

*Sepal width*.—6.0 mm.

*Sepal shape*.—Elliptical.

*Sepal apex*.—Convex.

*Sepal base*.—Acute.

*Length/width ratio*.—2.2.

*Flowering period*.—Primocane: Medium; July 1 to September 1. Floricane: Late; March 15 to April 30.

*Pedicel*.—Number of spines: Medium. Color: RHS 144A (Medium yellow-green). Anthocyanin coloration: Absent. Length: Medium, 2.76 mm. Diameter: 0.74 mm.

*Flower bud*.—Length: 2.3 mm. Diameter: 1.1 mm. Color: RHS 143C (Medium green).

Peduncle:

*Length*.—27.7 mm.

*Diameter*.—1.9 mm.

*Color*.—RHS 144A (Medium yellow-green).

*Presence of anthocyanin coloration*.—Absent.

*Intensity of anthocyanin coloration*.—Absent.

Fruit:

*Length*.—Long, 3.37 cm.

*Width*.—Medium, 3.01 cm.

*Ratio of length to width*.—1.1, as long as broad.

*Average number of drupelets per fruit*.—76.

*Weight (g/fruit)*.—Primocane: 6.5. Floricane: 5.6.

*Soluble solids (% in Brix)*.—10.7.

*Titratable acidity (% as citric acid)*.—10.6.

*Weight of seeds (mg/seed)*.—2.2.

*Size*.—From medium to large.

*Shape*.—Ovate (broad conical).

*Size of single drupelet*.—Large.

*Color*.—Immature fruit: RHS 43B (Medium red). Maturing fruit: RHS 45A (Dark red). Mature fruit color: RHS 46A (Dark red).

*Glossiness*.—Medium.

*Firmness*.—Medium.

*Adherence to plug*.—Medium.

*Main bearing type*.—Both on previous years cane in summer and on current years cane in autumn.

*Time of ripening*.—Primocane: Medium. Floricane: Late.

*Harvest season*.—Primocane: August 1 to October 15. Floricane: May 15 to July 1.

*Number of berries produced per node*.—2.

*Yield*.—High.

Disease resistance:

*Verticillium wilt*.—Susceptible.

*Cane botrytis*.—Highly susceptible.

*Orange rust*.—Highly susceptible.

Pest resistance/susceptibility: None observed.

COMPARISON WITH PARENTAL AND COMMERCIAL VARIETIES

'DrisRaspThree' differs from the proprietary female parent 'X146.7' (unpatented) in that 'DrisRaspThree' is higher in yield, has flavor, and a larger fruit size than 'X146.7'. Additionally, 'DrisRaspThree' has a more vigorous growth habit than 'X146.7'.

'DrisRaspThree' differs from the proprietary male parent 'S858.1' (unpatented) in that 'DrisRaspThree' is higher in yield and has a larger fruit size than 'S858.1'. Additionally, 'DrisRaspThree' has a more vigorous growth habit than 'S858.1'.

'DrisRaspThree' differs from the commercial variety 'Driscoll Maravilla' (U.S. Plant Pat. No. 14,804) in that 'DrisRaspThree' has berries with a medium firmness, while berries of 'Driscoll Maravilla' are firm. Additionally, 'DrisRaspThree' differs from 'Driscoll Maravilla' in that it has longer berries than the berries of 'Driscoll Maravilla'.

We claim:

1. A new and distinct variety of raspberry plant named 'DrisRaspThree' as described and shown herein.

* * * * *